(12) United States Patent
Gurjar et al.

(10) Patent No.: US 9,919,993 B2
(45) Date of Patent: Mar. 20, 2018

(54) PROCESS FOR PREPARATION OF ACITRECIN

(71) Applicant: EMCURE PHARMACEUTICALS LIMITED, Maharashtra (IN)

(72) Inventors: Mukund Keshav Gurjar, Maharashtra (IN); Shashikant Gangaram Joshi, Maharashtra (IN); Sachin Arvind Badhe, Maharashtra (IN); Mangesh Gorakhanath Kamble, Maharashtra (IN); Samit Satish Mehta, Maharashtra (IN)

(73) Assignee: Emcure Pharmaceuticals Limited, Maharashtra (IN)

( * ) Notice: Subject to any disclaimer, the term of this patent is extended or adjusted under 35 U.S.C. 154(b) by 0 days.

(21) Appl. No.: 15/512,316

(22) PCT Filed: Sep. 8, 2015

(86) PCT No.: PCT/IN2015/000350
§ 371 (c)(1),
(2) Date: Mar. 17, 2017

(87) PCT Pub. No.: WO2016/042573
PCT Pub. Date: Mar. 24, 2016

(65) Prior Publication Data
US 2017/0275229 A1  Sep. 28, 2017

(30) Foreign Application Priority Data

Sep. 17, 2014  (IN) .................. 2968/MUM/2014

(51) Int. Cl.
| | | |
|---|---|---|
| C07C 51/16 | (2006.01) |
| C07C 51/09 | (2006.01) |
| C07C 45/48 | (2006.01) |
| C07F 9/54 | (2006.01) |
| C07C 67/56 | (2006.01) |
| C07C 67/52 | (2006.01) |
| C07C 67/00 | (2006.01) |
| C07C 67/343 | (2006.01) |

(52) U.S. Cl.
CPC .............. *C07C 51/09* (2013.01); *C07C 45/48* (2013.01); *C07C 67/00* (2013.01); *C07C 67/343* (2013.01); *C07C 67/52* (2013.01); *C07C 67/56* (2013.01); *C07F 9/5456* (2013.01); *C07B 2200/13* (2013.01)

(58) Field of Classification Search
CPC ...................................................... C07C 51/09
USPC ........................................................ 562/407
See application file for complete search history.

(56) References Cited

U.S. PATENT DOCUMENTS

| | | |
|---|---|---|
| 4,225,527 A | 9/1980 | Bollag et al. |
| 8,835,680 B1 | 9/2014 | Deng et al. |

OTHER PUBLICATIONS

International Search Report issued in PCT/IN2015/000350, dated Feb. 4, 2016.

*Primary Examiner* — Deborah D Carr
(74) *Attorney, Agent, or Firm* — Seyfarth Shaw LLP

(57) ABSTRACT

The present invention provides a process for preparation of {(2E,4E,6E,8E)-9-(4-methoxy-2,3,6-trimethyl)phenyl-3,7-dimethyl-nona-2,4,6,8}tetraenoate, an acitretin intermediate of formula (VI) with trans isomer ≥97%, comprising of reacting 3-formyl-crotonic acid butyl ester of formula (V), substantially free of impurities, with 5-(4-methoxy-2,3,6-trimethylphenyl)-3-methyl-penta-2,4-diene-1-triphenyl phosphonium bromide of formula (IV) and isolating resultant compound of formula (VI), treating the filtrate with iodine for isomerization of the undesired cis intermediate and finally obtaining acitretin (I), with desired trans isomer ≥97%.

7 Claims, No Drawings

PROCESS FOR PREPARATION OF ACITRECIN

CROSS REFERENCE TO RELATED APPLICATIONS

This application is a national phase application under 35 U.S.C. § 371 of international Application No. PCT/IN2015/000350, filed on Sep. 8, 2015, which claims priority to Indian Patent Application No. 2968/MUM/2014, filed on Sep. 17, 2014; the disclosures of all of which are hereby incorporated by reference in their entirety.

FIELD OF THE INVENTION

The present invention relates to a process for the preparation of butyl {(2E,4E,6E,8E)-9-(4-methoxy-2,3,6-trimethyl)phenyl-3,7-dimethyl-nona-2,4,6,8}tetraenoate of formula (VI), a key intermediate of acitretin, comprising reaction of 5-(4-methoxy-2,3,6-trimethylphenyl)-3-methyl-penta-2,4-diene-1-triphenyl phosphonium bromide (IV) with 3-formyl-crotonic acid butyl ester (V) in presence of a mild inorganic base and isolating trans isomer of compound (VI), treating the filtrate with iodine for isomerization of undesired cis isomer to give trans isomer of compound of formula (VI). The process provides isomeric purity of ≥97% for compound (VI), which is instrumental in providing acitretin (I) conforming to regulatory specifications.

BACKGROUND OF THE INVENTION

Acitretin of formula (I), chemically known as (2E,4E,6E,8E)-9-(4-methoxy-2,3,6-trimethyl)phenyl-3,7-dimethyl-nona-2,4,6,8-tetraenoic acid, is a second generation retinoid approved by USFDA in 1996, for the treatment of psoriasis.

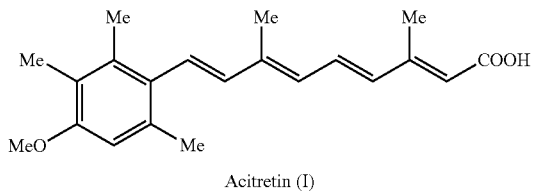 [SMILES: COc1cc(C)c(/C=C/C(C)=C/C=C/C(C)=C/C(=O)O)c(C)c1C]

Acitretin (I)

The process for preparation of acitretin (I) was first disclosed in U.S. Pat. No. 4,105,681 wherein the intermediate, 5-(4-methoxy-2,3,6-trimethylphenyl)-3-methyl-penta-2,4-diene-1-triphenyl phosphonium bromide was reacted with 3-formyl-crotonic acid butyl ester in presence of sodium hydride as base and dimethylformamide as solvent. The resultant ester derivative was obtained with a trans:cis (E/Z) ratio of around 55:45 which was subjected to hydrolysis in presence of potassium hydroxide and ethyl alcohol to obtain acitretin.

Use of hazardous, highly pyrophoric and moisture sensitive reagent like sodium hydride, along with cumbersome work-up and successive crystallizations to obtain the desired isomer rendered the process unviable for commercial scale.

Indian patent application 729/MUM/2012 discloses use of organic bases such as triethyl amine or pyridine for the reaction of 3-formyl-crotonic acid butyl ester and 5-(4-methoxy-2,3,6-trimethylphenyl)-3-methyl-penta-2,4-diene-1-triphenyl phosphonium bromide for the synthesis of acitretin. The process utilizes a large excess of the organic base (2.85:1.0) with respect to the reactant phosphonium bromide derivative. Further, there is no mention of the ratio of cis and trans geometric isomers of the product thus obtained either at the intermediate or final stage. The trans:cis (E/Z) ratio of the intermediate significantly impacts the final yield and purity of the product as several purifications and crystallizations are required to obtain the desired trans isomer.

The present inventors have experimentally observed that use of organic base in such large quantities severely hampers the removal of the undesired side product triphenyl phosphonium oxide formed in significant amounts. Also, the intermediate is obtained with a very modest trans:cis (E/Z) ratio.

WO2012/155796 discloses another method wherein alkali metal alkoxides are used as bases in the reaction of 5-(4-methoxy-2,3,6-trimethylphenyl)-3-methyl-penta-2,4-diene-1-triphenyl phosphonium bromide with 3-formyl-crotonic acid. The obtained reaction mass, after adjusting pH to 7-8 with acid, is directly subjected to catalytic isomerization using catalysts such as $Pd(OAc)_2$ or $Pd(NH_3)_2Cl_2$. The reaction mixture so obtained is quenched with water, neutralized and filtered to get the desired product, which is further recrystallized from ethyl acetate. Although this procedure avoids the hydrolysis step and attempts in-situ isomerization, however the use of expensive, soluble palladium catalyst which cannot be recycled from the reaction mass coupled with lengthy reaction time of 25-30 hours and large solvent volumes make the process unviable.

It may be noted that in the synthesis of acitretin, the key reaction of 5-(4-methoxy-2,3,6-trimethylphenyl)-3-methyl-penta-2,4-diene-1-triphenylphosphoniumbromide with 3-formyl crotonic acid or its ester in presence of either strong inorganic bases such as sodium hydride, alkali metal alkoxides or organic bases like triethylamine is common to almost all synthetic routes disclosed in the prior art. Hence, all these routes suffer from the inherent problems of formation of undesired impurities including cis-isomeric compounds and their separation from the desired all-trans product which necessitates various purification methods ranging from column chromatography, multiple crystallizations etc.

Thus, there still exists a need for a convenient, easy-to-scale up process for synthesis of acitretin (I) which avoids use of pyrophoric strong bases and provides a robust method which affords acitretin having desired isomeric purity in high yield.

The present inventors have developed a novel process for synthesis of acitretin (I) which not only avoids use of hazardous bases like sodium hydride but also provides a practical method comprising obtaining the ester intermediate (VI) with an enhanced E/Z ratio, and conversion of undesired cis-isomeric impurities into the desired all-trans isomer intermediate of acitretin, thereby increasing the overall yield of the final product (I).

In the present embodiment, 5-(4-methoxy-2,3,6-trimethylphenyl)-3-methyl-penta-2,4-diene-1-triphenyl phosphonium bromide of formula (IV) is reacted with 3-formyl-crotonic acid butyl ester (V) in presence of a mild inorganic base to give the corresponding ester intermediate (VI), which is isolated from the reaction mixture and the filtrate is treated with catalytic quantity of iodine, as a result of which the undesired cis isomeric impurities are converted to the desired all-trans ester derivative, butyl {(2E,4E,6E,8E)-9-(4-methoxy-2,3,6 trimethyl)phenyl-3,7-dimethyl-nona-2,4,6,8}tetraenoate of formula (VI). It should be noted that in the present invention, the undesired cis isomers of (VI), instead of being sent to effluent stream, are converted to the desired trans isomer to give the acitretin intermediate (VI) having the desired isomeric purity; resulting in significant yield enhancement. Further reaction of compound (VI) with alkali gives acitretin (I) of desired purity.

OBJECT OF THE INVENTION

An objective of the present invention is to provide acitretin of formula (I) having desired isomeric purity by a cost-effective and industrially viable process which does not involve hazardous hydride reagents, strong bases, or cumbersome separation procedures involving large volume of solvent/s.

Another object of the present invention is to provide an efficient and convenient process for preparation of acitretin (I) wherein the undesired cis-isomers at the penultimate stage are converted into the desired trans-compound and then hydrolyzed to acitretin, thereby resulting in significant improvement in the overall yield.

SUMMARY OF THE INVENTION

The present invention relates to a novel method for synthesis of (2E,4E,6E,8E)-9-(4-methoxy-2,3,6-trimethyl) phenyl-3,7-dimethyl-nona-2,4,6,8-tetraenoic acid of formula (I) having desired purity.

An aspect of the invention relates to a process for preparation of acitretin (I) comprising oxidation of L(+)-tartaric acid with sodium periodate followed by reaction with propionaldehyde in presence of piperidine to give 3-formyl-crotonic acid butyl ester of formula (V), which on subsequent reaction with 5-(4-methoxy-2,3,6-trimethylphenyl)-3-methyl-penta-2,4-diene-1-triphenyl-phosphonium bromide of formula (IV) in presence of sodium carbonate and solvent toluene gave trans isomer of butyl ester of {(2E,4E,6E,8E)-9-(4-methoxy-2,3,6-trimethyl)phenyl-3,7-dimethyl-nona-2,4,6,8} tetraenoate of formula (VI). Further isolation of the trans isomer and treatment of filtrate containing the cis isomer of compound of compound (VI) with iodine to give trans-ester of compound (VI) and subsequent treatment of compound (VI) with alkali hydroxide yielded acitretin of formula (I) having purity conforming to regulatory specifications.

The objectives of the present invention will become more apparent from the following detailed description.

DETAILED DESCRIPTION OF THE INVENTION

Acitretin, an aromatic analogue of retinoic acid related to retinol (vitamin A), is an important member of retinoid family, wherein the side chain comprises of nine carbon atoms, along with four double bonds. The carbon side chain is constructed during the reaction of 5-(4-methoxy-2,3,6-trimethylphenyl)-3-methyl-penta-2,4-diene-1-triphenyl-phosphonium bromide with 3-formyl crotonic acid or its ester, which is a key step in most of the synthetic sequences of acitretin, disclosed in the prior art. However, along with the formation of the desired trans isomer, this step also results in formation of undesired cis isomers, which are impurities, having structural similarities with trans isomer, viz. acitretin and its intermediates. They need to be removed from the desired product by successive purifications.

The present inventors, while developing an industrially applicable, economical process for acitretin, worked on the following grounds for overcoming the deficiencies encountered in prior art.

a) Controlling the formation of undesired cis-isomers in the synthesis of ester derivative (VI) which is the penultimate stage of acitretin synthesis, b) Isomerizing the undesired cis-isomeric impurities that were formed during coupling reaction to the corresponding trans-ester (VI) by a convenient and cost-effective process, c) Modifying the synthetic process for preparation of intermediate (VI), wherein the key reactant, 3-formyl crotonic acid butyl ester of formula (V) is prepared by a method which suppresses the formation of an unknown impurity. This impurity is difficult to remove and is further converted to an impurity having m/z: 396, based on mass spectroscopy, during the synthesis of acitretin in the final step.

While pursuing this goal, the present inventors have surprisingly found that when a mild base such as alkali metal carbonate was used in the reaction of 5-(4-methoxy-2,3,6-trimethylphenyl)-3-methyl-penta-2,4-diene-1-triphenyl phosphonium bromide (IV) with 3-formyl crotonic acid butyl ester (V), the undesired side reactions such as hydrolysis of ylide or Cannizzaro reaction which took place due to strong bases like alkali hydroxides were avoided. This resulted in control over impurity formation and a substantial increase in yield for the reaction as compared to prior art. Further, it was found that the trans:cis (E/Z) ratio in the resulting ester intermediate (VI) increased to 62:38 as against 54:46, which is disclosed in prior art. Further extensive experimentation aimed at conversion of cis-isomers obtained after isolation of first crop of compound (VI) led the present inventors to a process wherein significant portion of the cis-isomeric impurity at the penultimate ester stage in acitretin synthesis was isomerized using catalytic quantities of iodine to the desired all-trans ester compound.

In the present synthetic strategy, replacement of the moisture sensitive, hazardous bases such as sodium hydride, or strong alkali hydroxide bases with a mild inorganic base like sodium or potassium carbonate in the preparation of compound (VI) provided the ester compound with higher proportion of desired trans isomer. Also, the step of isomerization of cis-isomer from the filtrate or mother liquor after separation of ester derivative (VI) further increased the yield of required trans-ester compound and also the overall yield of acitretin (I), having desired isomeric and chemical purity.

Scheme 1: Method embodied in the present invention for the preparation of acitretin (I)

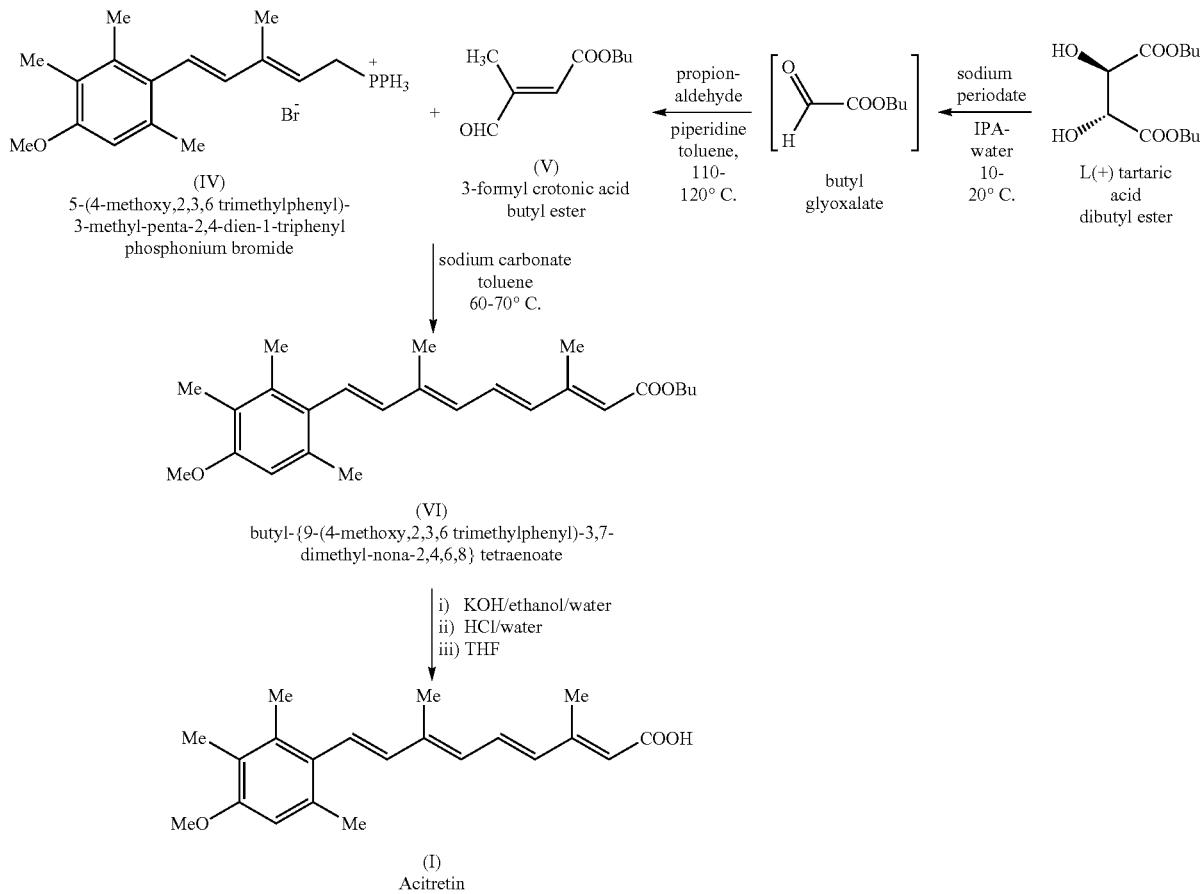

In an embodiment, 5-(4-methoxy-2,3,6-trimethylphenyl)-3-methyl-penta-2,4-diene-1-triphenyl phosphonium bromide of formula (IV) was treated with 3-formyl crotonic acid butyl ester (V) at 55-70° C. in presence of a mild base and an organic solvent to yield butyl {(2E,4E,6E,8E)-9-(4-methoxy-2,3,6-trimethyl)phenyl-3,7-dimethyl-nona-2,4,6,8} tetraenoate of formula (VI).

The organic solvent was selected from the group comprising of aromatic and aliphatic hydrocarbons such as ortho, meta, para xylenes, toluene, cyclohexane, n-hexane, n-heptane etc. The base was selected from carbonates of alkali metals such as sodium, potassium, lithium, cesium etc.

After completion of reaction as monitored by HPLC, the reaction mass was quenched with water, and the organic layer was separated and concentrated. The residue was triturated with heptane, filtered and the filtrate was stirred with aqueous methanol. The organic layer was separated and concentrated. The residue was crystallized from isopropanol and filtered to yield the first crop of compound (VI) with a yield in the range of 45 to 50%. The isomeric purity of the desired trans isomer was found to be ≥97%.

The filtrate containing the enriched cis isomers of compound (VI) was concentrated. The residue was dissolved in toluene and stirred with catalytic quantity of iodine at room temperature. The reaction mass thus obtained was washed with aqueous sodium thiosulfate followed by separation and concentration of the organic layer to give a residue, which was treated with isopropanol to yield the second crop of compound (VI). The yield was found to be in the range of 15 to 20% and the resulting trans isomer of (VI) had the purity of ≥97%. Thus the total yield of compound (VI) thus obtained was in the range 60 to 70% which apparently is around 30-40% higher than the yield reported in prior art.

The quantity of iodine used was in the range of 0.02 to 0.05 equivalent per mole of compound (IV) and played a significant role in converting the undesired cis isomer to the desired trans isomer. The compound of formula (VI) thus obtained had the desired trans isomer ≥97% and was found to provide Acitretin (I) conforming to regulatory specifications.

Compound (VI) was dissolved in ethanol and treated with aqueous potassium hydroxide solution at reflux temperature till completion of the reaction. After completion of the reaction, acitretin of formula (I) was found to separate out after water addition and neutralization of the reaction mass with hydrochloric acid. The mixture was cooled, filtered and optionally recrystallized from a solvent such as tetrahydrofuran to provide acitretin (I) having desired purity.

In a related embodiment, 3-formyl crotonic acid butyl ester of formula (V), which is one of the key reactants in the synthesis of acitretin, was synthesized as follows:

L-(+) tartaric acid dibutyl ester was treated with sodium periodate in aqueous isopropanol as solvent to give butyl glyoxylate which was further reacted with propionaldehyde using piperidine as a base. During synthesis of compound (V), use of piperidine as a base was found to have distinct advantages over the other bases reported in prior art as it suppressed the formation of an uncharacterized impurity which was relatively difficult to remove and subsequently led to another impurity in the final product and was found to persist even after repeated purifications. Removal of such impurity from the final product was a tedious task and repeated crystallizations were required to comply with regulatory specification, which resulted in considerable lowering of overall yield. Thus, by avoiding formation of the uncharacterized impurity, pure acitretin (I) could be obtained in high yield and purity.

When the compound (V) thus obtained was reacted with the phosphonium bromide derivative (IV), it gave the ester intermediate (VI), which was subsequently converted to acitretin, free from the impurity having m/z: 396, based on mass spectroscopy.

Compound (IV) was synthesized by following the procedures known in the art.
  a) reaction of 4-methoxy-2,3,6-trimethyl benzaldehyde with acetone in presence of sodium hydroxide to give 4-(4-methoxy-2,3,6-trimethylphenyl)-but-3-en-2-one (II)
  b) treatment of 4-(4-methoxy-2,3,6-trimethylphenyl)-but-3-en-2-one with vinyl magnesium bromide in a mixture of solvents, tetrahydrofuran and toluene to give 5-(4-methoxy-2,3,6-trimethylphenyl)-3-methyl-Penta-1,4-dien-3-ol, which was followed by reaction with triphenylphosphine hydrobromide.

The following examples are meant to be illustrative of the present invention. These examples exemplify the invention and are not to be construed as limiting the scope of the invention.

EXAMPLES

Example 1

Preparation of 4-(4-methoxy-2,3,6-trimethylphenyl)-but-3-en-2-one (II)

Acetone (6000 ml) was added to 4-methoxy-2,3,6 trimethyl benzaldehyde (500.3 g) and the mixture was stirred at 20-30° C. Aqueous solution of sodium hydroxide (134.8 g in 500 ml water) was gradually added to it and the resulting mixture was heated to 45-50° C. with continued stirring. After completion of the reaction, as monitored by HPLC, the reaction mass was cooled and acetic acid was added till pH 4.5 to 5.5. Distillation of acetone, followed by addition of cyclohexane to the residue, followed by washing with water, separation and concentration of the organic layer gave 4-(4-methoxy-2,3,6 trimethylphenyl)-but-3-en-2-one of formula (II).
Yield: 80-84%

Example 2

Preparation of 5-(4-methoxy-2,3,6-trimethylphenyl)-3-methyl-penta-2,4-diene-1-triphenyl phosphonium bromide (IV)

4-(4-Methoxy-2,3,6-trimethylphenyl)-but-3-en-2-one (II; 500 g) dissolved in toluene (2000 ml) was gradually added to a mixture of vinyl magnesium bromide (3500 ml; 1 molar solution in THF) and lithium chloride (4.8 g) and stirred at 20-30° C. till completion of the reaction as monitored by HPLC. The reaction mixture was quenched with water and concentrated hydrochloric acid was added till the pH was between 3 and 4. The organic layer was separated and concentrated to give residue containing 5-(4-methoxy-2,3,6 trimethylphenyl)-3-methyl-penta 1,4-dien-3-ol (III). Methyl isobutyl ketone (3500 ml) was added to the residue, followed by gradual addition of triphenyl phosphine hydrobromide (745.3 g) at room temperature. The reaction mixture was heated to 50-60° C. till completion of the reaction. The reaction mixture was cooled and filtered to give 5-(4-methoxy-2,3,6-trimethylphenyl)-3-methyl-penta-2,4-diene-1-triphenyl phosphonium bromide of formula (IV).
Yield: 1000 g (76%)

Example 3

Preparation of 3-formyl crotonic acid butyl ester (V)

Dibutyl-L-tartrate (500 g) was dissolved in isopropanol (3500 ml) at room temperature, and water (750 ml) was added to it. The reaction mixture was cooled to 15-25° C. and sodium metaperiodate (448.5 g) was gradually added to it with stirring. The reaction was continued at 20-30° C. till completion of the reaction based on GC analysis. The reaction mixture was filtered and the filtrate was concentrated. The resulting residue was dissolved in toluene (1000 ml), stirred and filtered to obtain the filtrate containing butyl glyoxylate. Propionaldehyde (221.0 g) was added to the filtrate and heated to around 60° C., followed by gradual addition of piperidine (26.4 g, dissolved in toluene). The reaction mixture was further heated and stirred at 110-120° C. till completion of the reaction, as monitored by GC. After completion, the reaction mass was cooled, washed with aqueous sulfuric acid, water and finally with aqueous sodium bicarbonate solution. The organic layer was concentrated and the residue was distilled to give 3-formyl crotonic acid butyl ester (V)
Yield: 230-280 g (35-43%)

Example 4

Preparation of butyl{(2E,4E,6E,8E)-9-(4-methoxy-2,3,6-trimethyl) phenyl-3,7-dimethyl-nona-2,4,6,8}tetraenoate (VI)

Sodium carbonate (297.1 g), was added to the mixture of 5-(4-Methoxy-2,3,6-trimethylphenyl)-3-methyl-penta-2,4-diene-1-triphenyl-phosphoniumbromide (IV; 1000 g) in toluene (5000 ml) followed by gradual addition of 3-formyl crotonic acid butyl ester (330 g) at room temperature. The stirred reaction mixture was heated to 60-70° C. till completion of the reaction as monitored by HPLC. The reaction mass was cooled, quenched with water. The organic layer was separated, concentrated and n-heptane was added to the residue. The mass was stirred, filtered and 40% aqueous methanol (2000 ml) was added to it with stirring. Layer separation, concentration of the organic layer, and crystallization of the resulting residue from isopropyl alcohol, optionally with seeding followed by filtration gave crop I of butyl {{(2E,4E,6E,8E)-9-(4-methoxy-2,3,6 trimethyl)phenyl-3,7 dimethyl-nona-2,4,6,8} tetraenoate (VI).
Yield: 45-50%;
Cis:Trans isomer ratio (2.0:98.0)

The filtrate was concentrated, the residue was dissolved in toluene (2000 ml) and treated with iodine (4.5 g) at room temperature. After completion of the reaction, as monitored by HPLC, the reaction mixture was stirred with aqueous sodium thiosulfate solution. Separation and concentration of the organic layer and crystallization of the resulting residue from isopropyl alcohol, optionally with seeding, gave crop II of butyl {{(2E,4E,6E,8E)-9-(4-methoxy-2,3,6-trimethyl) phenyl-3,7-dimethyl-nona-2,4,6,8} tetraenoate (VI).

Yield (crop II): 15 to 20%.
Cis:Trans isomer ratio (2.0:98.0)
Total yield (crop I+II): 60-70%.

Example 5

Preparation of acitretin (I)

Aqueous solution of potassium hydroxide (155.2 g in 600 ml water) was added to a solution of butyl {(2E,4E,6E,8E)-9-(4-methoxy-2,3,6-trimethyl) phenyl-3,7-dimethyl-nona-2,4,6,8}tetraenoate, VI (300.0 g) in ethanol (1800 ml) at 25-30° C. and the reaction mixture was stirred at reflux temperature till completion of the reaction. After completion, as monitored by HPLC, the reaction mixture was quenched with water, and hydrochloric acid was added till pH was between 2.5 and 3.5. The mass was heated at 70° C., stirred, cooled to 40-50° C. and filtered. Recrystallization of the resulting solid from tetrahydrofuran gave acitretin (I).

Yield: 154.0 g (60%)
Desired trans isomer: ≥98%

We claim:

1. A process for the preparation of acitretin of formula (I) comprising oxidation of L(+)-tartaric acid with sodium periodate followed by reaction with propionaldehyde in presence of piperidine to give 3-formyl-crotonic acid butyl ester of formula (V), which on subsequent reaction with 5-(4-methoxy-2,3,6-trimethylphenyl)-3-methyl-penta-2,4-diene-1-triphenyl phosphonium bromide of formula (IV) in presence of a base and an organic solvent provided the trans isomer of butyl {(2E,4E,6E,8E)-9-(4-methoxy-2,3,6-trimethyl)phenyl-3,7-dimethyl-nona-2,4,6,8} tetraenoate of formula (VI), which was isolated and the filtrate containing the cis isomer of compound of compound (VI) was treated with iodine to give the trans-ester of compound (VI), and subsequent treatment of the trans-ester of compound (VI) with alkali hydroxide provided acitretin of formula (I).

2. The method as claimed in claim 1, wherein the organic solvent is selected from the group of aromatic and aliphatic hydrocarbons comprising ortho xylene, meta xylene, para xylene, toluene, cyclohexane, n-hexane, and n-heptane or combinations thereof.

3. The method as claimed in claim 1, wherein the base is selected from the group of inorganic bases comprising sodium carbonate, lithium carbonate, potassium carbonate and cesium carbonate.

4. The method as claimed in claim 1, wherein the trans isomer of compound (VI) was isolated from the reaction mixture by quenching the mixture with water, concentrating the organic layer, triturating the resultant residue with heptane, filtering and concentrating the filtrate to provide a residue, which was treated with isopropanol and filtered to give trans isomer of compound (VI).

5. The method as claimed in claim 1, wherein the filtrate was concentrated, residue containing the cis isomer of compound (VI) was dissolved in toluene and treated with iodine, organic layer was concentrated, and residue was crystallized from isopropanol to provide the trans isomer of compound of formula (VI).

6. The method as claimed in claim 1, wherein the amount of iodine employed was in the range of 0.02 to 0.05 equivalent per mole of compound of formula (IV).

7. The method as claimed in claim 5, wherein the amount of iodine employed was in the range of 0.02 to 0.05 equivalent per mole of compound of formula (IV).

* * * * *